United States Patent [19]

Delony et al.

[11] Patent Number: 4,518,476

[45] Date of Patent: May 21, 1985

[54] END CLAMP FOR GEL SLAB PLATE ASSEMBLY

[75] Inventors: Timothy E. Delony, San Leandro; Daniel Y. M. Chu, San Francisco, both of Calif.

[73] Assignee: Bio-Rad Laboratories, Inc., Richmond, Calif.

[21] Appl. No.: 601,148

[22] Filed: Apr. 17, 1984

[51] Int. Cl.³ .......................... G01N 27/26; B25B 1/20
[52] U.S. Cl. .......................... 204/299 R; 204/180 G; 269/43; 269/234; 403/370; 403/374
[58] Field of Search .................. 204/180 G, 299 R; 403/368, 370, 374; 269/234, 43

[56] References Cited

U.S. PATENT DOCUMENTS

| 620,495 | 2/1899 | Ramseaur, Jr. | 269/234 |
| 3,826,483 | 7/1974 | Siegel | 269/234 |
| 3,932,265 | 1/1976 | Hoefer | 204/299 |
| 3,980,540 | 9/1976 | Hoefer | 204/180 |
| 4,208,045 | 6/1980 | Powe et al. | 269/234 |
| 4,224,134 | 9/1980 | Hoefer et al. | 204/299 |
| 4,292,161 | 9/1981 | Hoefer et al. | 204/299 |

FOREIGN PATENT DOCUMENTS

| 2016313 | 9/1979 | United Kingdom | 269/234 |
| 631298 | 11/1978 | U.S.S.R. | 269/234 |

OTHER PUBLICATIONS

F. W. Studier, "Analysis of Bacteriophage T7 Early RNAs and Proteins on Slab Gels", *J. Mol. Biol.*, (1973) 79, pp. 237–248.
H. Sauaia et al., "Vertical Slab Electrophoresis Apparatus", pp. 125–132.
W. B. Amos, "An Apparatus for Microelectrophoresis in Polyacrylamide Slab-Gels", Analytical Biochemistry, 70, pp. 612–615 (1976).
B. Sugden et al., "Agarose Slab-Gel Electrophoresis Equipment", *Analytical Biochemistry*, 68, pp. 36–46 (1975).

*Primary Examiner*—Howard S. Williams
*Assistant Examiner*—Terryence Chapman
*Attorney, Agent, or Firm*—Townsend and Townsend

[57] ABSTRACT

A novel device for clamping together a sandwich-type gel slab plate assembly includes an elongate housing having a recess on one side and two movable bars placed parallel to each other inside the recess. Due to a series of angled parallel surface segments on the lateral edges of the bars and one side wall of the recess, a vertical force against one bar translates into a lateral force against the other, urging the latter toward the other side wall of the recess, clamping the plates in between with even force along the entire length.

10 Claims, 3 Drawing Figures

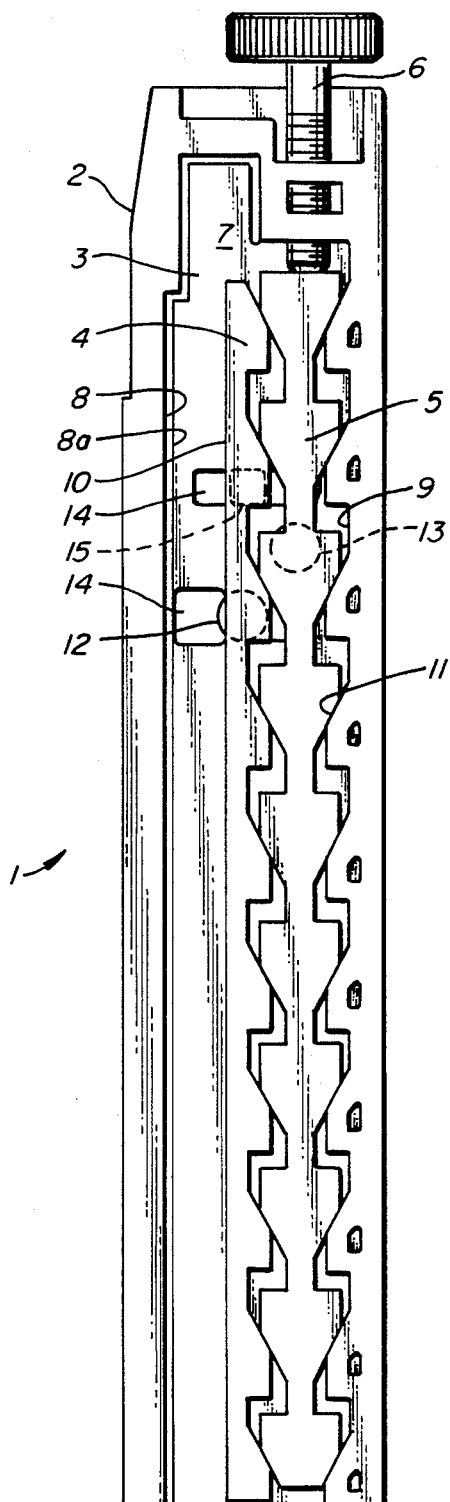
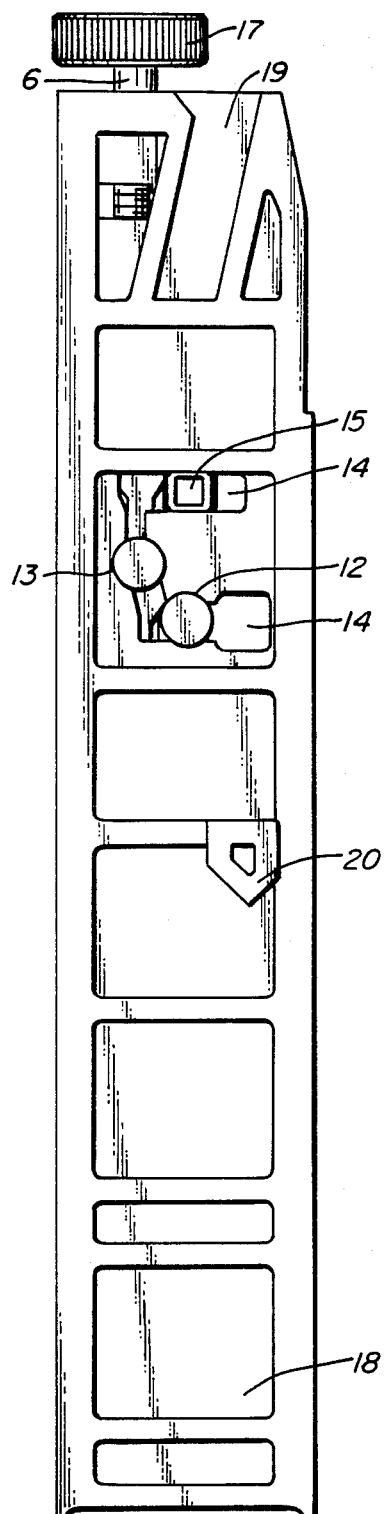
FIG._1    FIG._2.

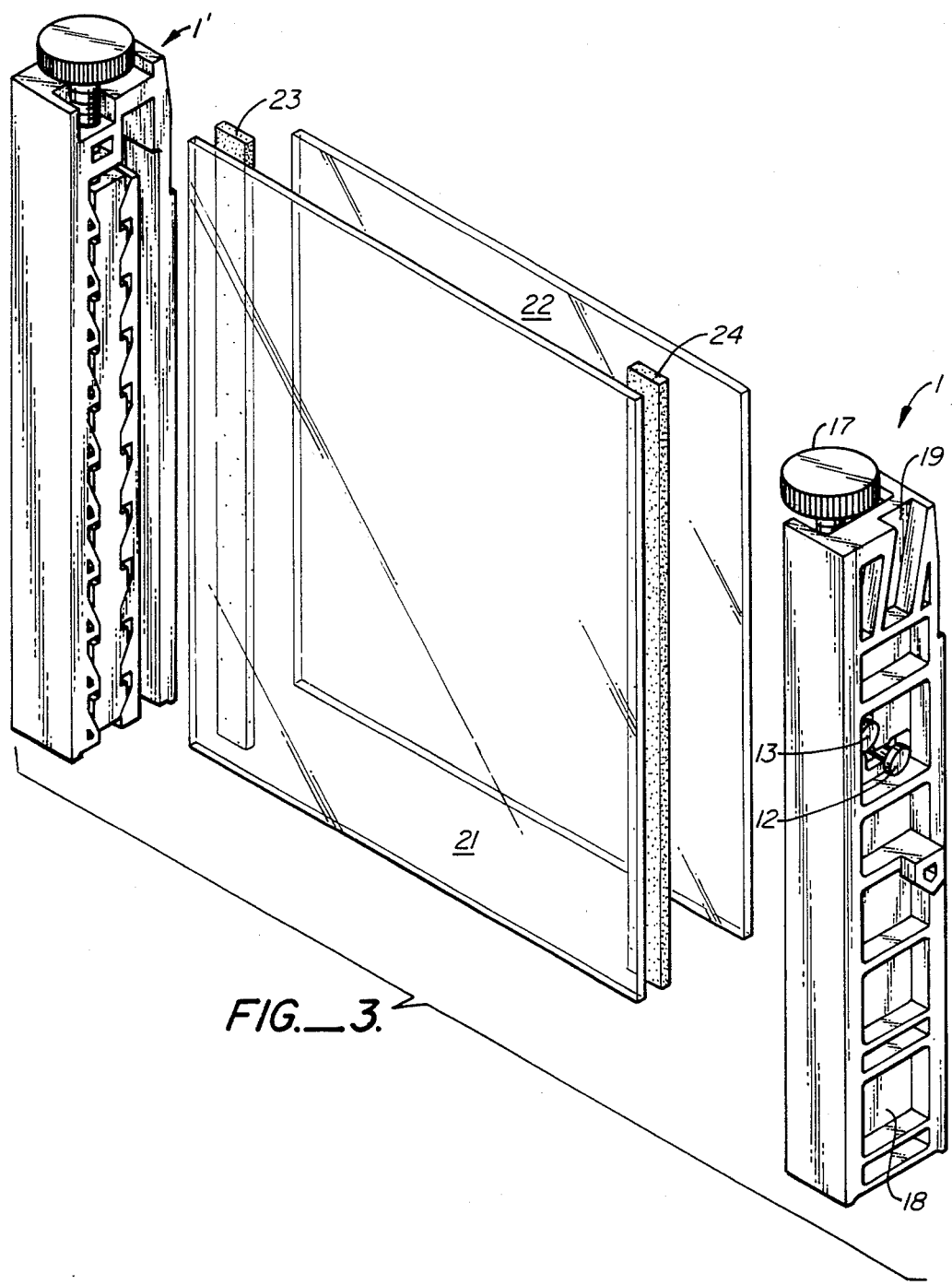
FIG._3.

END CLAMP FOR GEL SLAB PLATE ASSEMBLY

This invention relates to gel slab electrophoresis. In particular, this invention relates to a device for holding together a sandwich-type gel slab plate assembly.

BACKGROUND OF THE INVENTION

Gel electrophoresis is a widely used and highly effective technique for separating complex mixtures of chemical species. While the gels used in different types of electrophoresis apparatus may vary in shape, a common gel configuration is that of a thin flat slab. Gel slabs offer many advantages, including ease of evaluation by quantitative densitometry and photographic techniques, ease of drying and printing by autoradiography and other contact print methods, a geometry which permits improved heat dissipation and thus the opportunity for high voltage gradients, and the ability to perform simultaneous separations on a number of samples, for comparison as well as efficiency.

In many applications, the slab is most conveniently cast in a sandwich-type arrangement between two flat glass plates, and then used in an electrophoresis procedure while still held between the plates. Clear glass plates permit monitoring of the gel-forming solution as it is injected into the space between the plates, as well as monitoring of the finished slab and other adjacent portions of the entire apparatus while electrophoresis is taking place. The separation between the plates is typically maintained by spacer strips along the opposing vertical side edges. The entire assembly is held together by a clamp at each vertical edge. While the pressure exerted by the clamps must be tight enough to ensure a seal, it is frequently difficult to provide a pressure which is sufficiently even and controllable to reduce the danger of breakage of the glass.

SUMMARY OF THE INVENTION

The present invention resides in a novel design for an end clamp for a sandwich-type gel slab plate assembly, which clamp avoids localized stresses and provides a large degree of control to the operator. The clamp features an elongate housing with a recess and two movable bars positioned parallel to each other inside the recess. One of the bars moves laterally to press the plate edges between it and one side of the recess. The other bar moves vertically in the gap between the first bar and the opposite side of the recess, and has wedge-shaped sections which tend to widen the gap and thereby force the first bar against the plates. The wedges extend the entire length of the second bar on both sides with the effect of translating a longitudinal force on the second bar to a lateral force uniformly distributed along the length of the first bar. The result is an even pressure along the entire edge of the plate assembly, together with the ability to accommodate a wide range of sandwich thicknesses. The clamp can be tightened with a single screw, and the tension can be gradually and carefully applied with a high degree of control while still retaining the uniformity of pressure along the entire length of the plate assembly at each point in time. In a typical application, a pair of end clamps according to the invention is used, one for each vertical side of the plate assembly.

BRIEF DESCRIPTION OF THE DRAWINGS

FIG. 1 is an illustration of one embodiment of a clamp according to the present invention, showing the side facing the plate sandwich;

FIG. 2 illustrates the reverse side of the clamp of FIG. 1; and

FIG. 3 is an exploded perspective view of the entire gel slab plate assembly including the clamp of FIG. 1 and its mirror image.

DETAILED DESCRIPTION OF THE INVENTION AND PREFERRED EMBODIMENTS

The functional components of the clamp are illustrated in the example shown in FIG. 1, where the clamp itself is designated by the numeral 1, and its basic elements are a housing or shell 2 with a recess 3 on one side, two movable bars 4 and 5 inside the recess, and a screw 6 bearing down on one of the bars.

The recess has a flat back wall 7 and two side walls 8 and 9. In the embodiment shown, a small trough 8a is included in the backwall at the juncture between the back wall and the left side wall 8. This is included to ensure a sharp corner at the junction of walls 7 and 8. The clamp itself functions by receiving the plate sandwich assembly in the groove formed between the left side wall 8 of the recess and the opposing edge 10 of the adjacent bar 4, and by urging the bar toward the side wall to narrow the groove and force the intervening plates together.

As seen in FIG. 1, the position of the leftmost bar 4 (which may for convenience be termed the "clamping bar") as well as the force that this bar exerts against the glass plates is governed by the rightmost bar 5 (which may likewise be termed the "spreading bar"). The spreading bar in turn is controlled by the screw 6. During operation of the clamp, the longitudinal force exerted by the screw onto the spreading bar is translated into a lateral force on the clamping bar. This occurs by the interaction of the angled segments 11 on the two sides of the spreading bar with mating segments on the right side wall 9 of the recess and the right side of the clamping bar. In particular, the segments along any single edge are parallel to each other and spaced at intervals along the length of the edge. Those on one side of the spreading bar are at an angle which is equal but opposite to those on the other. A downward longitudinal force on the spreading bar thus causes it to act as a wedge which widens the gap between the clamping bar and the right side wall of the housing.

The actual angle of these angled surface segments may vary somewhat provided that it is the same for all segments. While the angle is not critical to the operation of the device, it will affect the extent to which the screw must be turned and the degree of force required to tighten down on the clamp. In general, an angle within the range of about 10° to about 45° with respect to the straight side wall of the recess will provide the best results. Preferred angles are those within the range of about 20° to about 30°. An angle of 25°39′ has been found to be particularly effective for plate assemblies of typical dimensions.

The drawings illustrate a preferred embodiment in which the angled surfaces in each series are arranged at regularly spaced intervals and are all of the same length. Furthermore, those on the clamping bar are in direct opposition to those on the right side wall of the recess.

The bars are held against the back wall 7 of the recess by protruding pins 12 and 13 which extend backward from the rear of the bars through a slot or elongated hole 14 passing through the back wall. The slot and pins are more clearly seen in FIG. 2 which shows the reverse side of the slab. Each of the pins 12 and 13 protrudes beyond the rear surface of the clamp housing and has a widened head to hold the pin in place inside the slot.

As shown in FIG. 2, the slot is shaped to permit the motion of each bar in its desired direction. Thus, the clamping bar is free to move in the lateral direction and the spreading bar in the downward direction at an angle equal to that of the angled surfaces. The latter direction is chosen so that when the screw is tightened down, the spreading bar will exert all its force against the angled surfaces of the recess side wall and the clamping bar rather than against the sides of the slot.

The clamping bar also has a second pin 15 which, although not of the locking type, further serves to guide the movement of the bar and provide uniform pressure by maintaining the bar parallel to the side walls of the recess.

A screw 6 passing through a threaded hole at the top of the clamp housing bears down upon the upper end of the spreading bar to provide the longitudinal force exerted against the angled surfaces. The screw has a knurled head 17 for manual operation to control the degree of force exerted.

The clamp housing shown in FIG. 2 contains a number of additional features not related to the clamping function itself but which render the device particularly useful in conjunction with other pieces of equipment used in a typical laboratory in connection with electrophoretic analysis. One example are the indentations 18 along the outer surface of the clamp housing. These indentations, particularly those toward the bottom, are functional in securing the bottom edge of the plate assembly against a flat surface with a gasket to seal off the lower boundary of the space between the plates. This is necessary when the plates are to be filled with gel-forming fluid to be then cast into a gel. The second indentation from the bottom is designed to meet with an eccentric cam on a post extending upward from a casting stand (neither the cam nor the stand are shown). Turning the cam forces the entire clamp downward to seal the plates against the base of the stand. Detailed descriptions of such cam and indentation arrangements are found in Hoefer, U.S. Pat. No. 3,932,265 (Jan. 13, 1976) and Hoefer et al., U.S. Pat. No. 4,292,161 (Sept. 29, 1981).

Further additional features are the angled channel 19 at the upper end of the outer clamp surface and the protruding lug 20 at about the midpoint of the clamp. The channel and lug are functional in securing the gel plate assembly to an electrophoresis cell. A detailed description of these elements and their functions is found in commonly assigned copending application, entitled "Apparatus for Vertical Gel Slab Electrophoresis", Ser. No. 601,193, filed on the same date as the present application.

The material of construction for the clamp housing, bars and screw is not critical, provided that it is rigid, non-conductive, easily machined or molded and with a slight degree of resiliency to enhance control of the force applied during clamping. Polymeric resins are particularly convenient.

In typical use, the clamp of the present invention is paired with a second clamp to secure together a rectangular plate sandwich at opposite sides. The clamps are retained in place during both the gel formation and the electrophoresis procedures.

FIG. 3 illustrates the entire assembly in an exploded view. The clamps 1 and 1' are mirror images of each other. Although this is not strictly necessary, it is convenient for purposes relating to the additional features on the outer face of the clamp housing, as referred to above. The plates 21 and 22 are separated by spacers 23 and 24 which define the thickness of the gel slab. The plates may be of equal height, or unequal height (the latter shown), straight-edged (as shown) or notched. Examples of notched plates are those manufactured by Hoefer Scientific Instruments, San Francisco, Califor., as part of its Vertical Slab Electrophoresis Unit SE-500; and those disclosed by F. W. Studier in "Analysis of Bacteriophage T7 Early RNAs And Protein On Slab Gels," *J. Mol. Biol.*, 79, 237–248 (1973). The shape of the clamp housing recess in which the plate edges are inserted will be adapted to the plate dimensions.

The foregoing description is intended primarily for purposes of illustration. The invention as a whole is not intended to be limited to the particular structural or operational features described above. Numerous modifications and variations, still falling within the spirit and scope of the invention, will be readily apparent to those skilled in the art.

What is claimed is:

1. A device for clamping together a plurality of plates along at least a portion of one edge of each with substantially uniform pressure, which comprises:
    a housing having on one side thereof an elongate recess defined by a substantially flat back wall and first and second side walls, said first side wall being flat and said second side wall containing a plurality of parallel flat segments located at intervals along the length thereof, each segment facing at an angle with respect to said first side wall;
    a first elongate bar movably mounted within said recess, having a first side facing said first side wall and a second side facing said second side wall, said first side being flat and parallel to said first side wall to define therewith a groove for receiving said plates, and said second side containing a plurality of parallel flat segments located at intervals along the length thereof, each segment facing at an angle equal but opposite to that of said parallel flat segments of said second side wall;
    means for restricting the movement of said first elongate bar to a direction perpendicular to said first side wall;
    a second elongate bar movably mounted within said recess between said first elongate bar and said second side wall of said recess, each side surface of said second elongate bar containing a plurality of parallel flat segments at angles and intervals indentical to those of the opposing segments on said first elongate bar and said second side wall of said recess, respectively; and
    means for urging said second elongate bar lengthwise to urge said parallel flat segments on each side thereof against said parallel flat segments of said first elongate bar and said parallel flat segments of said second side wall of said recess, respectively, and thereby urge said first elongate bar toward said first side wall of said recess.

2. A device according to claim 1 in which said parallel flat angled segments of said second recess side wall and said second side of said first elongate bar are at regular intervals.

3. A device according to claim 1 in which said parallel flat angled segments of said second recess side wall directly face said parallel flat angled segments on said second side of said first elongate bar and are at regular intervals.

4. A device according to claim 1 in which the angle which said parallel flat segments of said second recess side wall form with said first recess side wall is from about 10° to about 45°.

5. A device according to claim 1 in which the angle which said parallel flat segments of said second recess side wall form with said first recess side wall is from about 20° to about 30°.

6. A device according to claim 1 further comprising means for restricting the movement of said second bar to a direction parallel to said parallel flat segments of said second side wall of said recess.

7. A device according to claim 1 further comprising means for maintaining said first bar parallel to said first side wall of said recess.

8. A device according to claim 1 in which said urging means are comprised of a screw mounted in said housing at one end of said recess bearing on one end of said second elongate bar.

9. A sandwich-type gel slab plate assembly comprising:
   a pair of flat rectangular glass plates of equal width with side edges in alignment;
   a pair of flat spacer bars disposed between said plates, one said bar aligned with each side edge of said plates; and
   a pair of clamping devices according to claims 1, 2, 3, 4, 5, 6, 7 or 8, each said device clamping inside its respective groove said glass plates along one side edge thereof over one said spacer.

10. A device for clamping together a plurality of plates along at least a portion of one edge of each with substantially uniform pressure, which comprises:

a housing having on one side thereof an elongate recess defined by a substantially flat back wall and first and second side walls, said first side wall being flat and said second side wall containing a plurality of parallel flat segments located at regular intervals along the length thereof, each segment facing at an angle of from about 20° to about 30° with respect to said first side wall;

a first elongate bar movably mounted within said recess, having a first side facing said first side wall and a second side facing said second side wall, said first side being flat and parallel to said first side wall to define therewith a groove for receiving the edges of said plates, and said second side containing a plurality of parallel flat segments directly facing said second recess side wall segments and at an angle equal but opposite to that of said parallel flat segments of said second side wall;

means for restricting the movement of said first elongate bar to a direction perpendicular to said first side wall and for maintaining said first elongate bar parallel to said first side wall of said recess;

a second elongate bar movably mounted within said recess between said first elongate bar and said second side wall of said recess, each side surface of said second elongate bar containing a plurality of parallel flat segments at angles and intervals identical to those of the opposing segments on said first elongate bar and said second side wall of said recess, respectively;

means for restricting the movement of said second elongate bar to a direction parallel to said parallel flat segments of said second side wall of said recess; and means for urging said second elongate bar lengthwise to urge said parallel flat segments on each side thereof against said parallel flat segments of said first elongate bar and said parallel flat segments of said second side wall of said recess, respectively, and thereby urge said first elongate bar toward said first side wall of said recess.

* * * * *